United States Patent
Fei et al.

(10) Patent No.: US 11,278,478 B2
(45) Date of Patent: Mar. 22, 2022

(54) ORAL CARE COMPOSITIONS AND METHODS FOR INCREASING STABILITY OF THE SAME

(71) Applicant: Colgate-Palmolive Company, New York, NY (US)

(72) Inventors: Lin Fei, Kendall Park, NJ (US); Prakasarao Mandadi, Flemington, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 365 days.

(21) Appl. No.: 15/756,146

(22) PCT Filed: Dec. 13, 2017

(86) PCT No.: PCT/US2017/066032
§ 371 (c)(1),
(2) Date: Feb. 28, 2018

(87) PCT Pub. No.: WO2019/117885
PCT Pub. Date: Jun. 20, 2019

(65) Prior Publication Data
US 2019/0175466 A1    Jun. 13, 2019

(51) Int. Cl.
| | |
|---|---|
| *A61K 8/34* | (2006.01) |
| *A61K 8/81* | (2006.01) |
| *A61K 8/90* | (2006.01) |
| *A61K 8/22* | (2006.01) |
| *A61Q 11/00* | (2006.01) |
| *A61Q 11/02* | (2006.01) |

(52) U.S. Cl.
CPC .............. *A61K 8/345* (2013.01); *A61K 8/22* (2013.01); *A61K 8/8158* (2013.01); *A61K 8/8182* (2013.01); *A61K 8/90* (2013.01); *A61Q 11/00* (2013.01); *A61Q 11/02* (2013.01); *A61K 2800/30* (2013.01); *A61K 2800/31* (2013.01); *A61K 2800/42* (2013.01); *A61K 2800/48* (2013.01)

(58) Field of Classification Search
CPC ........ A61K 8/22; A61K 8/345; A61K 8/8182; A61K 8/8158; A61K 8/90; A61K 2800/31; A61K 2800/42; A61K 2800/48; A61K 2800/30; A61Q 1/00; A61Q 11/02
See application file for complete search history.

(56) References Cited

U.S. PATENT DOCUMENTS

| | | | |
|---|---|---|---|
| 7,534,272 B2 | 5/2009 | Cassier et al. | |
| 8,591,868 B2 | 11/2013 | Chopra et al. | |
| 2005/0142154 A1 | 6/2005 | Blatt et al. | |
| 2007/0183988 A1 | 8/2007 | Prosise et al. | |
| 2008/0213730 A1* | 9/2008 | Prencipe ............ | A61C 19/066 433/216 |
| 2012/0308499 A1 | 12/2012 | Vic et al. | |
| 2014/0147402 A1 | 5/2014 | Klug et al. | |
| 2017/0027849 A1 | 2/2017 | Midha et al. | |

FOREIGN PATENT DOCUMENTS

| | | |
|---|---|---|
| EP | 1506771 | 2/2005 |
| WO | 2012/123241 | 9/2012 |

OTHER PUBLICATIONS

Joiner et al.: Tooth colour and whiteness: A review: https://www.sciencedirect.com/science/article/pii/S0300571217302324?via%3Dihub, available online Sep. 18, 2017. retrieved on Jun. 19, 2019.*
International Search Report and Written Opinion of the International Searching Authority in International Application No. PCT/US2017/066032, dated Jun. 29, 2018.

* cited by examiner

*Primary Examiner* — Hong Yu

(57) ABSTRACT

Anhydrous oral care compositions and methods for preventing phase separation in the anhydrous oral care composition are disclosed. The oral care composition may include an orally acceptable vehicle, a thickening system, and a whitening agent. The orally acceptable vehicle may include propylene glycol, and the thickening system may include a polymeric thickener. The polymeric thickener may be or include a copolymer of 2-acrylamidomethylpropanesulphonic acid or a salt thereof.

16 Claims, No Drawings

ORAL CARE COMPOSITIONS AND METHODS FOR INCREASING STABILITY OF THE SAME

CROSS-REFERENCE TO RELATED APPLICATIONS

This application is the U.S. National Phase under 35 USC 371, and claims the benefit of and priority to, International Application No. PCT/US2017/066032 filed Dec. 13, 2017, the contents of which are incorporated herein in their entirety.

BACKGROUND

Conventional oral care products or compositions thereof (e.g., toothpastes, gels, etc.) including whitening agents are often utilized to whiten teeth. For example, conventional toothpastes including peroxides (e.g., hydrogen peroxide) are often utilized to oxidize chromophores bound to surfaces of teeth to thereby whiten the teeth. The peroxides, however, are often unstable and subject to degradation. As such, the peroxides are often incorporated into non-aqueous oral care products and/or compositions to aid in stabilizing the peroxides. While non-aqueous oral care compositions, such as non-aqueous toothpastes, have proven to be effective for stabilizing the peroxides, gelling agents and/or thickeners that are compatible with propylene glycol are limited.

In view of the foregoing, non-aqueous oral care compositions incorporating hydrogen peroxide often utilize a limited selection of conventional thickeners to facilitate the thickening and/or gelling of the oral care compositions. For example, the non-aqueous oral care compositions often incorporate fumed silica and/or cross-linked polymers (e.g., cross-linked PVP) to thicken and/or gel the oral care compositions. The conventional thickeners, however, are not able to form networks with one another. As such, solids contained in the oral care compositions may often settle, thereby resulting in phase separation within the oral care corn positions.

What is needed, then, are improved non-aqueous oral care compositions incorporating a whitening agent and methods for preventing phase separation therein.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an anhydrous oral care composition including an orally acceptable vehicle, a thickening system, and a whitening agent. The orally acceptable vehicle may include propylene glycol, and the thickening system may include an polymeric thickener that may be a copolymer of 2-acrylamidomethylpropanesulphonic acid or a salt thereof.

In at least one implementation, the polymeric thickener may be a block copolymer.

In another implementation, the polymeric thickener may include a block copolymer of a first monomer and a second monomer. The first monomer may include the 2-acrylamidomethylpropanesulphonic acid or a salt thereof, and the second monomer may include a vinyl monomer having a nitrogenous side chain.

In another implementation, the vinyl monomer may be or include at least one of a methacrylic acid, a methacrylate, a methacrylamide, a methacrylate salt, a vinyl pyrrolidone, and combinations thereof.

In another implementation, the first monomer may be an ammonium salt of 2-acrylamidomethylpropanesulphonic acid.

In another implementation, the second monomer ay include a vinyl monomer having an amide functional group.

In another implementation, the second monomer may be N-vinylpyrrolidone.

In another implementation, the polymeric thickener may be a copolymer of an ammonium salt of 2-acrylamidomethylpropanesulphonic acid and a N-vinylpyrrolidone.

In another implementation, the thickening system may include or consist of a copolymer of an ammonium salt of 2-acrylamidomethylpropanesulphonic acid and a N-vinylpyrrolidone.

In another implementation, the anhydrous oral care composition may be substantially free of fluoride.

In another implementation, the anhydrous oral care composition may not include or be free of fumed silica and cross-linked polyvinylpyrrolidone.

In another implementation, the oral care composition may include less than 5.0 weight % water, preferably less than 1.0 weight %) water, and more preferably less than 0.1 weight % water.

In another implementation, the whitening agent may include a cross-linked polyvinylpyrrolidone (PVP) hydrogen peroxide complex.

The foregoing and/or other aspects and utilities embodied in the present disclosure may be achieved by providing a method for preventing phase separation in an anhydrous oral care composition. The method may include contacting an orally acceptable vehicle including propylene glycol and a whitening agent with one another to form the oral care composition, and contacting the anhydrous oral care composition with a polymeric thickener.

In at least one implementation, the polymeric thickener may include a block copolymer of a first monomer and a second monomer, wherein the first monomer may include an acrylamide having a sulfonic group, and wherein the second monomer may include a vinyl monomer having a nitrogenous side chain, preferably, the polymeric thickener is a copolymer of an ammonium salt of 2-acrylamidomethylpropanesulphonic acid and a N-vinylpyrrolidone Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Compositions

The present inventors have surprisingly and unexpectedly discovered that polymers or polymeric thickeners effectively prevent phase separation in oral care compositions incorporating whitening agents (e.g., peroxides). The polymeric thickener may be or include a copolymer of a first monomer, such as a 2-acrylamidomethylpropanesulphonic acid or a salt thereof, and a second monomer, such as a methacrylic acid, methacrylates, methacrylamides, methacrylate salts, and vinylpyrrolidone, effectively prevents phase separation in oral care compositions incorporating whitening agents (e.g., peroxides). Particularly, the present inventors have surprisingly and unexpectedly discovered that a block copolymer of a 2-acrylamidomethylpropanesulphonic acid salt and N-vinylpyrrolidone effectively prevents phase separation in non-aqueous oral care compositions incorporating whitening agents (e.g., peroxides). The present inventors have also surprisingly and unexpectedly discovered that the block copolymer of a 2-acrylamidomethylpropanesulphonic acid salt and N-vinylpyrrolidone is an effective thickener for non-aqueous oral care compositions. The present inventors have further surprisingly and unexpectedly discovered that the block copolymer of a 2-acrylamidomethylpropanesulphonic acid salt and N-vinylpyrrolidone is compatible with and/or maintains stability of the whitening agents of the oral care compositions. It was further surprisingly and unexpectedly discovered that the oral care composition exhibited stability (e.g., no phase separation) for at least two months when exposed to accelerated aging conditions.

Compositions disclosed herein may be or include an oral care product and/or an oral care composition thereof. The oral care composition may be a non-aqueous oral care composition, such as a non-aqueous dentifrice or toothpaste. The oral care composition may include an orally acceptable vehicle, such as propylene glycol, one or more whitening agents, and a thickener. In at least one implementation, the thickener of the oral care composition does not include fumed silica and/or a cross-linked polymer, such as cross-linked polyvinylpyrrolidone.

The oral care composition prior to use may be anhydrous. For example, the oral care composition may be free or substantially free of water. As used herein, "free" or "substantially free" may refer to a composition that contains less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the oral care composition. The oral care composition prior to use may have a "low water content". As used herein, "low water content" may refer to a composition that contains greater than about 5 weight % and less than about 7 weight % or less than about 10 weight %.

Orally Acceptable Vehicle

The oral care composition may form at least a portion of or be used in one or more oral care products. Illustrative oral care products may include, but are not limited to, a toothpaste (dentifrice), a prophylactic paste, a tooth powder, a paste tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may form at least a portion of or be used with a toothpaste. For example, the oral care composition may typically be a gel of the toothpaste, or a whitening gel to be combined with the toothpaste. The oral care composition may include or be combined with an orally acceptable vehicle to form the oral care product (e.g., the toothpaste). In an exemplary implementation, the orally acceptable vehicle may be or include propylene glycol.

In at least one implementation, the orally acceptable vehicle may include one or more humectants. Illustrative humectants may be or include, but are not limited to, glycerin, propylene glycol, and combinations thereof. In a preferred implementation, the orally acceptable vehicle may be or includes, but is not limited to, propylene glycol. The propylene glycol may be present in an amount of from 20 weight % to about 75 weight %, based on a total weight of the oral care composition. For example, the propylene glycol may be present in an amount of from about 20 weight %, about 25 weight %, about 30 weight %, about 35 weight %, about 40 weight %, or about 45 weight % to about 50 weight %, about 55 weight %, about 60 weight %, about 65 weight %, about 70 weight %, or about 75 weight %. In another example, the propylene glycol may be present in an amount of from about 20 weight % to about 75 weight %, about 25 weight % to about 70 weight %, about 30 weight % to about 65 weight %, about 35 weight % to about 60 weight %, about 40 weight % to about 55 weight %, or about 45 weight % to about 50 weight %. In a preferred embodiment, the propylene glycol may be present in an amount of about 45 weight % to about 50 weight %, or in an amount of about 60 weight % to about 70 weight %.

Whitening Agent

The oral care composition may include one or more whitening agents. The whitening agents may be or include, but are not limited to, hydrogen peroxide or one or more sources of hydrogen peroxide. For example, the whitening agents may be hydrogen peroxide and/or hydrogen peroxide releasing substances. The one or more sources of hydrogen peroxide may be or include any compound or material configured to release hydrogen peroxide. Preferably, the whitening agents include, but are not limited to, solid whitening agents and bound whitening agents which are substantially anhydrous oxygen generating compounds. Solid whitening agents useful herein include peroxides, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts. The sources of hydrogen peroxide or whitening agents may also be or include, but are not limited to, PEROXYDONE™ XL 10 complex or POLYPLASDONE® XL 10F, which are commercially available from Ashland Inc. of Covington, Ky. In a typical implementation, the source of hydrogen peroxide includes a cross-linked PVP hydrogen peroxide complex.

The amount or concentration of the source of hydrogen peroxide may vary widely. In at least one example, the source of hydrogen peroxide may be present in an amount that provides a concentration of hydrogen peroxide of less than or equal to 4 weight %, less than or equal to 3.5 weight %, less than or equal to 3 weight %, less than or equal to 2.5 weight less than or equal to 2 weight %, or less than or equal to 1.5 weight %, based on a total weight of the oral care composition. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 1 weight %, about 3 weight %, about 5 weight %, about 7 weight %, about 9 weight %, about 11 weight %, about 13 weight %, or about 15 weight % to about 17 weight %, about 19 weight %, about 21 weight about 22 weight %, about 23 weight %, about 25 weight %, about 27 weight %, about 29 weight %, or about 30 weight %. In another example, the source of hydrogen peroxide may be present in an amount of from about 1 weight % to about 30 weight %, about 3 weight % to about 29 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In other embodiments, the source of hydrogen peroxide is a cross-linked PVP complexed with hydrogen peroxide, and is present in an amount of from about 15 weight % to about 17 weight %, preferably about 16 weight % to about 17 weight %, and more preferably about 16.5 weight %. In further embodiments, the source of hydrogen peroxide is a cross-linked PVP complexed with hydrogen peroxide, and is present in an amount of from about 20 weight % to about 30 weight %, preferably about 21 weight % to about 25 weight %, and more preferably about 22 weight %.

Thickening System

The oral care composition may include a thickening system having one or more thickeners. The one or more thickeners may be any orally acceptable thickener or thickening agent configured to at least partially form a network and thereby prevent phase separation in the oral care composition. Illustrative thickeners may be or include a polymeric thickener, such as a copolymer of at least two monomers, where a first monomer may be an acrylamide having a sulfonic or sulphonic group, and a second monomer may be a vinyl monomer having a nitrogenous side chain. Illustrative vinyl monomers may be or include, but are not limited to, methacrylic acid, methacrylates, methacrylamides, methacrylate salts, vinyl pyrrolidone, and the like, and combinations thereof. For example, the thickener may be or include a copolymer of 2-acrylamidomethylpropanesulphonic acid or a salt thereof, such as an ammonium or sodium salt, and a vinyl monomer having a nitrogenous cyclic side chain or a vinyl monomer having an amide functional group, such as N-vinylpyrrolidone. In a preferred implementation, the thickener may be a copolymer of the ammonium salt of 2-acrylamidomethylpropanesulphonic acid and N-vinylpyrrolidone, which is commercially available as ARISTOFLEX® AVC from Clariant International Ltd. of Charlotte, N.C. The block copolymer thickener may have the INCI name ammonium acryloyldimethyltaurate/VP copolymer or correspond to the GAS reference number 335383-60-3. Another preferred thickener may be a block copolymer of the sodium salt of 2-acrylamidomethylpropanesulphonic acid and N-vinylpyrrolidone, which is commercially available as ARISTOFLEX® AVS from Clariant International Ltd. of Charlotte, N.C., and has the INCI name sodium acryloyldimethyltaurate/VP crosspolymer. In yet another preferred implementation, the polymeric thickener may be ARISTOFLEX® HMB, ARISTOFLEX® BLV, and/or ARISTOFLEX® TAC, which are commercially available from Clariant International Ltd. In a further preferred implementation, the polymeric thickener may be or include polyacrylate crosspolymer-6, which is commercially available as SEPIMAX™ ZEN from SEPPIC S.A., a subsidiary of the Air Liquide group, Puteaux Cedex, France.

In at least one implementation, the oral care composition may be free or substantially free of fumed silica. In another implementation, the oral care composition prior to use may be free or substantially free of cross-linked PVP. It should be appreciated that in at least one implementation, the oral care composition prior to use may include a cross-linked PVP complexed with hydrogen peroxide as a source of hydrogen peroxide, but may also be free or substantially free of the cross-linked PVP. In yet another implementation, the oral care composition may be free or substantially free of both fumed silica and cross-linked PVP prior to use. In yet another implementation, the oral care composition may include fumed silica and cross-linked PVP.

The amount or concentration of the thickening system or the thickener thereof in the oral care composition may vary widely. In at least one implementation, the amount of the thickener present in the oral care composition may be greater than or equal to 0.1 weight % and less than or equal to 1.0 weight %, based on a total weight of the oral care composition. For example, the amount of the thickener present in the oral care composition may be from about 0.1 weight %, about 0.2 weight %, about 0.3 weight %, about 0.4 weight %, or about 0.5 weight % to about 0.6 weight %, about 0.7 weight %, about 0.8 weight %, about 0.9 weight %, or about 1.0 weight %. In another example, the amount of the thickener present in the oral care composition may be from about 0.1 weight % to about 1.0 weight %, about 0.2 weight % to about 0.9 weight %, about 0.3 weight % to about 0.8 weight %, about 0.4 weight % to about 0.7 weight %, or about 0.5 weight % to about 0.6 weight %. In some embodiments, the amount of the thickener present in the oral care composition may be from about 0.4 weight % to about 0.6 weight %, optionally about 0.4 weight % or about 0.55 weight %.

In another implementation, the amount of the thickener present in the oral care composition may be greater than 0 weight % and less than or equal to 20 weight %, based on a total weight of the oral care composition. For example, the amount of the thickener present in the oral care composition may be greater than 0 weight % and less than or equal to 20 weight %, less than or equal to 18 weight %, less than or equal to 16 weight %, less than or equal to 14 weight %, less than or equal to 12 weight %, less than or equal to 10 weight %, less than or equal to 8 weight %, less than or equal to 6 weight %, less than or equal to 5 weight %, less than or equal to 4 weight %, less than or equal to 3 weight %, less than or equal to 2 weight %, less than or equal to 1.8 weight %, less than or equal to 1.6 weight %, less than or equal to 1.4 weight %, less than or equal to 1.2 weight %, less than or equal to 1.0 weight %, less than or equal to 0.8 weight %, less than or equal to 0.6 weight %, or less than or equal to 0.4 weight %.

In at least one implementation, the oral care composition may include additional and/or optional thickeners. Illustrative additional or optional thickeners may be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations thereof.

Polymers

In at least one implementation, the oral care composition may include one or more polymers or polymer additives. For example, the oral care composition may include one or more block co-polymers of polyethylene glycol and polyethylene glycol (e.g., molecular weight of at least 5000 Da), polypropylene glycol and polyethylene glycol, and the like, and combinations thereof. In at least one implementation, the oral care composition includes a block co-polymer of ethylene oxide and propylene oxide represented by the formula (1),

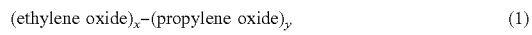

$$(\text{ethylene oxide})_x-(\text{propylene oxide})_y \qquad (1)$$

where x is an integer from about 80 to about 150 (e.g., x=100-130, or about 118), and y is an integer from about 30 to about 80 (e.g., y=60-70, or about 66). The block co-polymer of ethylene oxide and propylene oxide may have an average molecular weight greater than or equal to about 5,000 Da and less than or equal to about 20,000 Da. For example, the molecular weight of the block co-polymer of ethylene oxide and propylene oxide may be from about 8,000 Da to about 13,000 Da. In another example, the molecular weight of the block co-polymer of ethylene oxide and propylene oxide may be from about 9,800 Da or about 10,000 Da. In yet another example, the molecular weight of the block co-polymer of ethylene oxide and propylene oxide may be from about 8,000 Da to about 10,000 Da. In at least one implementation, the oral care composition does not include a block co-polymer of ethylene oxide and propylene oxide having a molecular weight less than 5,000 Da. For example, at least 99.5%, at least 99.0%, or at least 99.9% of the block co-polymer of ethylene oxide and propylene oxide present in the oral care composition has a molecular weight greater than or equal to 5,000 Da. In at least one implementation, the polymers or polymer additives, if included in the composition, may be or include PLURAFLO® L4370 and PLURAFLO® L1220, both of which are commercially available from BASF of Wyandotte, Mich.

The amount or concentration of the polymers or polymer additives (e.g., block co-polymers) present in the oral care composition may vary widely. In at least one implementation, the amount of the polymers or polymer additives (e.g., block co-polymers) present in the oral care composition may be from about 5 weight % to about 10 weight %. For example, the amount of the polymers or polymer additives (e.g., block co-polymers) present in the oral care composition may be from about 5.0 weight %, about 5.5 weight %, about 6.0 weight %, about 6.5 weight %, about 7.0 weight %, or about 7.5 weight to about 8.0 weight %, about 8.5 weight %, about 9.0 weight %, about 9.5 weight %, or about 10.0 weight %. In another example, the amount of the polymers or polymer additives present in the oral care composition may be from about 5.0 weight % to about 10.0 weight %, about 5.5 weight % to about 9.5 weight %, about 6.0 weight % to about 9.0 weight %, about 6.5 weight % to about 8.5 weight %, or about 7.0 weight % to about 8.0 weight %. In another implementation, the amount of the polymer or polymer additives present in the oral care composition may be from about 5 weight % to about 15 weight % based on a total weight of the oral care composition. For example, the amount of the polymers or polymer additives (e.g., block co-polymers) present in the oral care composition may be from about 5.0 weight %, about 5.5 weight %, about 6.0 weight %, about 6.5 weight %, about 7.0 weight %, about 7.5 weight %, about 8.0 weight %, about 8.5 weight %, about 9.0 weight %, about 9.5 weight %, or about 10.0 weight % to about 10.5 weight %, about 11.0 weight %, about 11.5 weight %, about 12.0 weight %, about 12.5 weight %, about 13.0 weight %, about 13.5 weight %, about 14.0 weight %, about 14.5 weight or about 15.0 weight %.

In at least one implementation, the polymers or polymer additives may be or include PLURACARE® L1220, which is commercially available from BASF of Wyandotte, Mich. In another implementation, the polymer or polymer additive may be or include polyethylene glycol (e.g., about 400-800 Da, or about 600 Da). In yet another implementation, the polymer or polymer additive may be or include a low or medium molecular weight polyethylene glycol having a molecular weight greater than or equal to about 400 Da and less than or equal to about 1000 Da. For example, the polymer or polymer additive may be or include PEG 400, PEG 600, PEG 800, PEG 100, and the like, and mixtures or combinations thereof. In at least one implementation, the oral care composition may include a stabilizing amount of an additional linear PVP.

Surfactants or Surface Active Agents

The oral care composition may include a surfactant or surfactant system including one or more surfactants. The surfactant may be configured to at least partially aid or facilitate the mixing or contact between one or more components of the oral care composition. For example, the surfactant may aid the mixing or facilitate contact between a hydrophobic component/phase and a hydrophilic component/phase of the oral care composition. The surfactants may be or include anionic, nonionic, cationic, amphoteric surfactants, or combinations thereof.

Illustrative surfactants may be or include, but are not limited to, water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate, and sodium dodecyl benzenesulfonate, and cocoamidopropyl betaine. Illustrative surfactants or surface active agents may also be or include, but are not limited to, PLURONIC® L35, PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, PLURONIC® P105, and the like, and combinations thereof, which are commercially available from BASF of Mount Olive, N.J. In a typical implementation, the surfactant is or includes a polyethylene glycol)-block-poly(propylene glycol)-block-poly(ethylene glycol) or PEG-PPG-PEG (PLURONIC® L-35).

The amount of the surfactants present in the oral care composition may vary widely. In at least one implementation, the amount of one or more surfactants present in the oral care composition may be greater than or equal to 0.0 weight % and less than or equal to 10.0 weight %, based on a total weight of the oral care composition. For example, the amount of the surfactant present in the oral care composition may be from about 0.0 weight %, about 1 weight %, about 2 weight %, about 3 weight %, about 4 weight %, or about 4.5 weight % to about 5.5 weight %, about 6 weight %, about 7 weight %, about 8 weight %, about 9 weight %, or about 10 weight %, based on a total weight of the oral care composition. In another example, the amount of the surfactant present in the oral care composition may be from about 0.0 weight % to about 10 weight %, about 1 weight % to about 9 weight %, about 2 weight % to about 8 weight %, about 3 weight % to about 7 weight %, about 4 weight % to about 6 weight %, or about 4.5 weight % to about 5.5 weight %, based on a total weight of the oral care composition. In a preferred implementation, the amount of the surfactant present in the oral care composition may be from about 4 weight % to about 6 weight %, more preferably about 4.5 weight % to about 5.5 weight %, more preferably about 5.0 weight %, based on a total weight of the oral care composition.

Abrasives

In at least one implementation, the oral care composition may include one or more abrasives or dental abrasive agents. As used herein, the term "abrasive" may also refer to materials commonly referred to as "polishing agents".

Any suitable orally acceptable abrasive may be used, but preferably, the type, fineness (particle size) and amount of the abrasives should be selected such that tooth enamel is not excessively abraded in normal use of the oral care composition.

Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, (3-calcium pyrophosphate, tricalcium phosphate, calcium polymetaphosphate and insoluble sodium polymetaphosphate. Average particle size of an abrasive, if present, is generally about 0.1 to about 30 μm, for example about 1 to about 20 μm or about 5 to about 15 μm. In at least one implementation, the abrasive may be maintained in the dentifrice of the oral care composition.

In at least one implementation, the amount or concentration of the abrasives may be from about 5 wt % to about 40 wt %, based on a total weight of the oral care composition. For example, the amount of the abrasives present in the oral care composition may be from about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 10.5 wt %, about 11.0 wt %, about 11.5 wt %, or about 12.0 wt % to about 12.5 wt %, about 13.0 wt %, about 13.5 wt %, about 14.0 wt %, about 14.5 wt %, about 15.0 wt %, about 15.5 wt %, about 16.0 wt %, about 16.5 wt %, about 17.0 wt %, about 17.5 wt %, about 18.0 wt %, about 18.5 wt %, about 19.0 wt %, about 19.5 wt %, or about 20.0 wt %. In another example, the amount of the abrasives present in the oral care composition may be from about 5 wt %, about 10 wt %, about 15 wt %, or about 20 wt % to about 25 wt %, about 30 wt %, about 35 wt %, or about 40 wt %.

Fluoride Ion Source

In at least one implementation, the oral care products and/or the oral care composition thereof may be free or substantially free of fluoride (e.g., soluble fluoride salts). In another implementation, the oral care products and/or the oral care composition thereof may further include fluoride, such as one or more fluoride ion sources (e.g., soluble fluoride salts), A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium fluoride. The amount of the fluoride ion source in the oral care composition may be less than 0.08 wt %, less than 0.07 wt %, less than 0.06 wt %, less than 0.05 wt %, or less than 0.04 wt %. For example, the amount of the fluoride ion source may be about 0.05 wt %. In another implementation, the fluoride ion source is present in an amount to provide a total of about 100 to about 20,000 ppm, about 200 to about 5,000 ppm, or about 500 to about 2,500 ppm, fluoride ions.

Additional Ingredients

It should be appreciated to one having ordinary skill in the art, that the oral care products and/or the oral care composition thereof may include other additional ingredients/components. For example, the oral care products and/or the oral care composition thereof may include anti-caries agents, desensitizing agents, viscosity modifiers, diluents, modifying agents, humectants, mouth feel agents, sweetening agents, flavor agents, colorants, preservatives, and the like, and combinations and mixtures thereof. In some embodiments, the compositions described herein are substantially free of volatile flavoring agents. In other embodiments, the compositions described herein are completely free of volatile flavoring agents. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent, Generally, anticalculus agents may not be compatible with some oral care composition, however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

Methods

The present disclosure may provide methods for preventing phase separation in an oral care product or the oral care composition thereof that incorporate whitening agents (e.g., peroxides). The method may include contacting the oral care composition with a polymeric thickener having a first monomer, such as a 2-acrylamidomethylpropanesulphonic acid or a salt thereof, and a second monomer, such as a methacrylic acid, methacrylates, methacrylamides, methacrylate salts, and vinylpyrrolidone. The oral care composition may be a non-aqueous or propylene glycol based oral care composition. The method may include not combining at least one other thickener, such as fumed silica and cross-linked polyvinylpyrrolidone. The method may also include forming a intermolecular bonding network between a plurality of the polymers of the polymeric thickener to prevent phase separation. The method may include preventing phase separation under accelerated aging conditions, for example at a temperature from about 40° C. to about 50° C. The method may include preventing phase separation for at least two months under accelerated aging conditions. The method may further include maintaining viability, stability, and/or compatibility with the whitening agent under accelerated aging conditions. For example, the method may include maintaining viability, stability, and/or compatibility with the whitening agent for at least three months.

Example

The following example and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

A control composition (1) and two exemplary compositions of the present invention (2) and (3), are evaluated. All three compositions were prepared by combining the ingredients/components according to Table 1, in accordance with methods known to those skilled in the art. All three compositions contained hydrogen peroxide, as delivered from a cross-linked PVP complexed with hydrogen peroxide. As illustrated in Table 1, the control composition (1) contained fumed silica and polyvinylpyrrolidone (PVP) as the thickener, and the exemplary compositions of the present invention (2) and (3) contained only the copolymer of the ammonium salt of 2-acrylamidomethylpropanesulphonic acid and N-vinylpyrrolidone as the thickener.

The stability of compositions (1)-(3) were evaluated by observing phase separation under accelerated aging conditions (at about 50° C.) for two months, and assigning a score on a scale of 0 to 4 to the observed phase separation. A score of '0' indicated no separation, a score of "1" indicated trace amount separation, a score of "2" indicated slight separation, a score of "3" indicated moderate separation, and a score of '4' indicated failure or separation. The results of the stability are summarized in Table 2.

TABLE 1

Control (1) and Exemplary Whitening Compositions (2) and (3)

| Material | Control (1) Wt. % | Ex. (2) Wt. % | Ex. (3) Wt. % |
| --- | --- | --- | --- |
| Propylene glycol | 48.76 | 52.96 | 67.75 |
| Sodium metaphosphate | 15.00 | 15.00 | — |
| Polyethylene glycol/polypropylene glycol copolymer | 7.50 | 7.50 | 7.50 |
| Copolymer of ammonium salt of 2-acrylamidomethylpropanesulphonic acid and N-vinylpyrrolidone | — | 0.55 | 0.40 |
| Cross-linked PVP complexed with hydrogen peroxide | 16.50 | 16.50 | 22.00 |
| Polyvinylpyrrolidone | 2.00 | — | — |
| Fumed silica | 2.75 | — | — |
| Other (e.g. flavor, colorants, etc.) | 3.13 | 3.13 | 0.85 |
| Pyrophosphates (e.g. TSPP and/or SAPP) | 1.60 | 1.60 | 0.50 |
| Sodium lauryl sulfate | 2.00 | 2.00 | 1.00 |
| Fluoride source | 0.76 | 0.76 | — |
| Total | 100 | 100 | 100 |

TABLE 2

Formulation Separation Rating after Aging at 49° C. for 2 months

| Control (1) | Exemplary Composition (2) | Exemplary Composition (3) |
| --- | --- | --- |
| 2 | 0 | 0 |

As indicated in Table 2, the control composition (1) exhibited phase separation and received a phase separation score of 2, while the exemplary compositions of the present invention (2) and (3) exhibited no phase separation and received a score of 0. Without being bound by theory, it is believed that the intermolecular network formed between the polymers of the block-copolymer in the exemplary compositions of the present invention (2) and (3), at least partially prevented solids from "settling," and thus, prevented phase separation.

The viability, stability, and/or compatibility of the polymeric block copolymer thickener with the whitening agent of the exemplary compositions of the present invention (2) and (3) were also evaluated under accelerated aging conditions (at 40° C.) for at least three months. The results are summarized in Table 3.

TABLE 3

Recovery of Peroxide from Exemplary Composition (2) and (3) after Aging at 40° C. for 3 months

| | Time | | |
| --- | --- | --- | --- |
| | 0 Weeks | Aged | Recovery |
| Control (1) | 2.99 | 2.70 | 90.3% |
| Ex. (2) | 3.01 | 2.94 | 97.7% |
| Ex. (3) | 4.01 | 4.00 | 99.8% |

As indicated in Table 3, about 98% peroxide was recovered after exposing the exemplary compositions of the present invention (2) and (3) to accelerated aging conditions for at least three months. This demonstrated that the polymeric block copolymer thickener was compatible with the whitening agent, and maintained the viability and stability of the whitening agent.

The present disclosure has been described with reference to exemplary implementations, Although a limited number of implementations have been shown and described, it will be appreciated by those skilled in the art that changes may be made in these implementations without departing from the principles and spirit of the preceding detailed description, it is intended that the present disclosure be construed as including all such modifications and alterations insofar as they come within the scope of the appended claims or the equivalents thereof.

What is claimed is:

1. An anhydrous dentifrice or toothpaste, comprising:
   an orally acceptable vehicle, the orally acceptable vehicle comprising propylene glycol;
   a thickening system, the thickening system comprising a polymeric thickener, wherein the polymeric thickener is a copolymer of 2-acrylamidomethylpropanesulphonic acid or a salt thereof; and
   a peroxide whitening agent.

2. The anhydrous dentifrice or toothpaste of claim 1, wherein the polymeric thickener is a block copolymer.

3. The anhydrous dentifrice or toothpaste of claim 1, wherein the polymeric thickener comprises a block copolymer of a first monomer and a second monomer,
   wherein the first monomer comprises the 2-acrylamidomethylpropanesulphonic acid or a salt thereof, and
   wherein the second monomer comprises a vinyl monomer having a nitrogenous side chain.

4. The anhydrous dentifrice or toothpaste of claim 3, wherein the vinyl monomer is at least one of a methacrylic acid, a methacrylate, a methacrylamide, a methacrylate salt, and a vinyl pyrrolidone.

5. The anhydrous dentifrice or toothpaste of claim 4, wherein the first monomer is an ammonium salt of 2-acrylamidomethylpropanesulphonic acid.

6. The anhydrous dentifrice or toothpaste of claim 3, wherein the second monomer comprises a vinyl monomer having an amide functional group.

7. The anhydrous dentifrice or toothpaste of claim 6, wherein the second monomer is N-vinylpyrrolidone.

8. The anhydrous dentifrice or toothpaste of claim 1, wherein the polymeric thickener comprises a copolymer of an ammonium salt of 2-acrylamidomethylpropanesulphonic acid and a N-vinylpyrrolidone.

9. The anhydrous dentifrice or toothpaste of claim 1, wherein the thickening system consists of a copolymer of an ammonium salt of 2-acrylamidomethylpropanesulphonic acid and a N-vinylpyrrolidone.

10. The anhydrous dentifrice or toothpaste of claim 1, wherein the polymeric thickener is present in an amount of from about 0.1 wt. % to about 1 wt. %, of the anhydrous oral care composition.

11. The anhydrous dentifrice or toothpaste of claim 1, wherein the polymeric thickener is present in an amount of from about 0.25 wt. % to about 0.75 wt. %, optionally 0.4 wt. % or 0.55 wt. %, of the anhydrous oral care composition.

12. The anhydrous dentifrice or toothpaste of claim 1, wherein the anhydrous oral care composition is substantially free of fluoride, and optionally fluoride free.

13. The anhydrous dentifrice or toothpaste of claim 1, wherein the anhydrous oral care composition does not comprise fumed silica and/or cross-linked polyvinylpyrrolidone.

14. The anhydrous dentifrice or toothpaste of claim 1, wherein the oral care composition comprises less than 5.0 weight % water, preferably less than 1.0 weight % water, and more preferably less than 0.1 weight % water.

15. The anhydrous dentifrice or toothpaste of claim 1, wherein the whitening agent comprises a cross-linked polyvinylpyrrolidone (PVP) hydrogen peroxide complex.

16. A method for whitening a tooth of a subject need thereof, comprising: contacting an oral cavity surface of said subject with an anhydrous oral care composition according to claim 1.

* * * * *

UNITED STATES PATENT AND TRADEMARK OFFICE
CERTIFICATE OF CORRECTION

PATENT NO. : 11,278,478 B2
APPLICATION NO. : 15/756146
DATED : March 22, 2022
INVENTOR(S) : Lin Fei et al.

It is certified that error appears in the above-identified patent and that said Letters Patent is hereby corrected as shown below:

In the Specification

In Column 1, Line 41, delete "corn positions." and insert -- compositions. --, therefor.

In Column 2, Line 14, delete "ay" and insert -- may --, therefor.

In Column 10, Line 54, before "modifying", insert -- pH --.

In Column 13, Lines 31-32, delete "description, it" and insert -- description. It --, therefor.

Signed and Sealed this
Thirty-first Day of May, 2022

Katherine Kelly Vidal
*Director of the United States Patent and Trademark Office*